(12) United States Patent
Chen

(10) Patent No.: US 8,450,651 B2
(45) Date of Patent: May 28, 2013

(54) HUMAN SKIN MASK HEATING/WARMING DEVICE

(76) Inventor: Eric Chen, New Taipei (TW)

( * ) Notice: Subject to any disclaimer, the term of this patent is extended or adjusted under 35 U.S.C. 154(b) by 27 days.

(21) Appl. No.: 13/092,368

(22) Filed: Apr. 22, 2011

(65) Prior Publication Data

US 2012/0193344 A1    Aug. 2, 2012

(30) Foreign Application Priority Data

Feb. 2, 2011  (TW) .............................. 100202466 U

(51) Int. Cl.
*F27D 11/00* (2006.01)
(52) U.S. Cl.
USPC ............... 219/385; 219/443.1; 219/452.13; 219/453.13; 219/450.1; 219/524; 99/426; 99/427; 99/324; 99/331; 99/339
(58) Field of Classification Search
USPC ............. 219/443.1, 452.13, 453.13, 450.1, 219/524, 385; 99/426, 427, 430, 431, 432, 99/433, 439, 324, 331, 339, 340, 372, 402; 2/206
See application file for complete search history.

(56) References Cited

U.S. PATENT DOCUMENTS

| 4,011,431 | A | * | 3/1977 | Levin ............................ 219/524 |
| 4,532,414 | A | * | 7/1985 | Shah et al. .................... 392/470 |
| 5,736,714 | A | * | 4/1998 | Bechtold, Jr. ................. 219/521 |
| 6,466,737 | B1 | * | 10/2002 | Birdsell et al. ................ 392/367 |
| 7,274,003 | B2 | * | 9/2007 | Baumann ...................... 219/401 |
| 2002/0043529 | A1 | * | 4/2002 | Pickering et al. ......... 219/452.13 |
| 2003/0167556 | A1 | * | 9/2003 | Kelley ............................. 2/206 |
| 2003/0205567 | A1 | * | 11/2003 | McConnell et al. ........... 219/385 |

* cited by examiner

*Primary Examiner* — Tu B Hoang
*Assistant Examiner* — Amit K Singh
(74) *Attorney, Agent, or Firm* — Guice Patents PLLC

(57) ABSTRACT

A human skin mask heating/warming device includes a case and an electrical heating device. The case includes an upper casing and a lower casing. One end of the upper casing is pivotally connected with one end of the lower casing. The upper and lower casings can be opened/closed to enclose a mask (pack) in the case. Alternatively, the case is integrally formed with the upper and lower casings or the upper and lower casings are integrally assembled with each other to form the case. One side of the case is formed with a slot or slit. The mask (pack) can be guided into the case through the slot or slit. The electrical heating device includes an electrical unit and a heating unit. The electrical unit provides a current to the heating unit for generating heat. The heating unit is disposed on the case for providing heat to the mask (pack).

9 Claims, 5 Drawing Sheets

HUMAN SKIN MASK HEATING/WARMING DEVICE

BACKGROUND OF THE INVENTION

1. Field of the Invention

The present invention relates generally to a device for heating a human skin mask, and more particularly to a human skin mask heating/warming device capable of heating/warming various human skin masks (packs) such as facemasks (packs), eye masks (packs) and breast masks (packs).

2. Description of the Related Art

Various skin masks such as facemasks are commercially available nowadays. It is known that such skin masks are generally made of wood pulp, cotton material, silk cotton or unwoven fabrics. The skin mask is shaped with a configuration of a face, eyes, T-shape or any other suitable body shape by means of pressing. The current facemasks and other skin masks in the market can be classified into two types according to their usages as follows:

The skin masks of one type are pure membranes. In use, it is necessary to first apply a maintenance product to the face or the skin of a body and then overlay the membrane on the face or the skin of the body. In this case, the skin can absorb the water or nutrients of the maintenance product to clean and maintain the skin.

The skin masks of the other type are membranes already painted with a maintenance product. Such skin mask is packaged in a tin foil-made pack. In use, a user only needs to open the tin foil-made pack to overlay the skin mask with the maintenance product on the face or the skin of the body to clean and maintain the skin.

In the case that the skin mask is preheated, the pores of the skin can be expanded to achieve better cleaning and maintaining effect. In general, a tin foil-made pack with a skin mask inside is nothing more than heated by means of a hairdryer or by means of soaking the tin foil-made pack into hot water. This is not only quite inconvenient, but also can hardly precisely control the temperature. As a result, the original function of the skin mask may be reduced.

SUMMARY OF THE INVENTION

It is therefore a primary object of the present invention to provide a human skin mask heating/warming device, which is able to more conveniently and better heat/warm various human skin masks.

It is a further object of the present invention to provide the above human skin mask heating/warming device, which is able to heat/warm various human skin masks in accordance with the requirements of different maintenance solutions.

To achieve the above and other objects, the human skin mask heating/warming device of the present invention includes a case and an electrical heating device. The case includes an upper casing and a lower casing. One end of the upper casing is pivotally connected with one end of the lower casing. The upper and lower casings can be opened/closed relative to each other to enclose a mask (pack) in the case. Alternatively, the case is integrally formed with the upper and lower casings or the upper and lower casings are integrally assembled with each other to form the case. One side of the case is formed with a slot or slit. The mask (pack) can be guided into the case through the slot or slit. The electrical heating device includes an electrical unit and a heating unit. The electrical unit provides a current to the heating unit for generating heat. The heating unit is disposed on the case for providing heat to the mask (pack).

The present invention can be best understood through the following description and accompanying drawings, wherein:

DETAILED DESCRIPTION OF THE PREFERRED EMBODIMENTS

Figure 1:
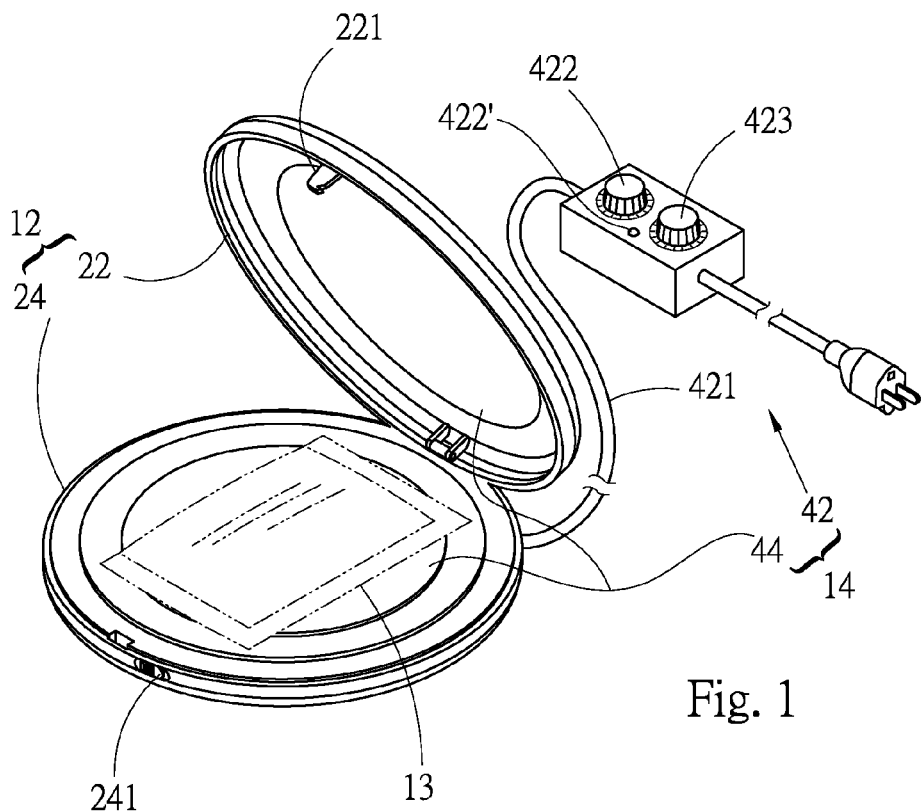
FIG. 1 is a perspective view of a first embodiment of the present invention.

Please refer to FIG. 1. According to a first embodiment, the human skin mask heating/warming device of the present invention includes a case 12 and an electrical heating device 14.

The case 12 includes an upper casing 22 and a lower casing 24.

One end of the upper casing 22 is pivotally connected with one end of the lower casing 24. Accordingly, the upper and lower casings 22, 24 can be pivotally opened/closed relative to each other to enclose a human skin mask (pack). The upper casing 22 is provided with an insertion pin 221, while the lower casing 24 is provided with an engagement plate 241. The insertion pin 221 can be engaged with a first end of the engagement plate 241. A second end of the engagement plate 241 extends out of a lateral side of the lower casing 24. A user can shift the engagement plate 241 to release the insertion pin 221 for opening the case 12 to place in or take out the mask (pack) 13. The case 12 can receive one or several or up to 100 masks (packs) 13.

The electrical heating device 14 is disposed on the case 12, at least including an electrical unit 42 and a heating unit 44.

The electrical unit 42 provides a current to the heating unit 44 for generating heat. The electrical unit 42 includes a power cable 421 connected to civil power supply. Alternatively, the electrical unit 42 has the function of voltage and current regulation for providing suitable voltage and current to the heating unit 44.

The electrical unit 42 further includes a temperature controller 422 such as a rotary button for controlling or regulating the temperature of the heating unit 44.

The electrical unit 42 further includes a time controller 423 such as a rotary button for controlling heating time of the heating unit 44.

The heating unit 44 is disposed on the upper casing 22 and the lower casing 24 for providing heat to the mask (pack) 13. In this embodiment, the heating unit 44 is a resistive electrical heating pad disposed on an inner face of the upper casing 22 and/or an inner face of the lower casing 24. The resistive electrical heating pad is in contact with the mask (pack) 13 to provide better heat conduction effect.

Figure 2:
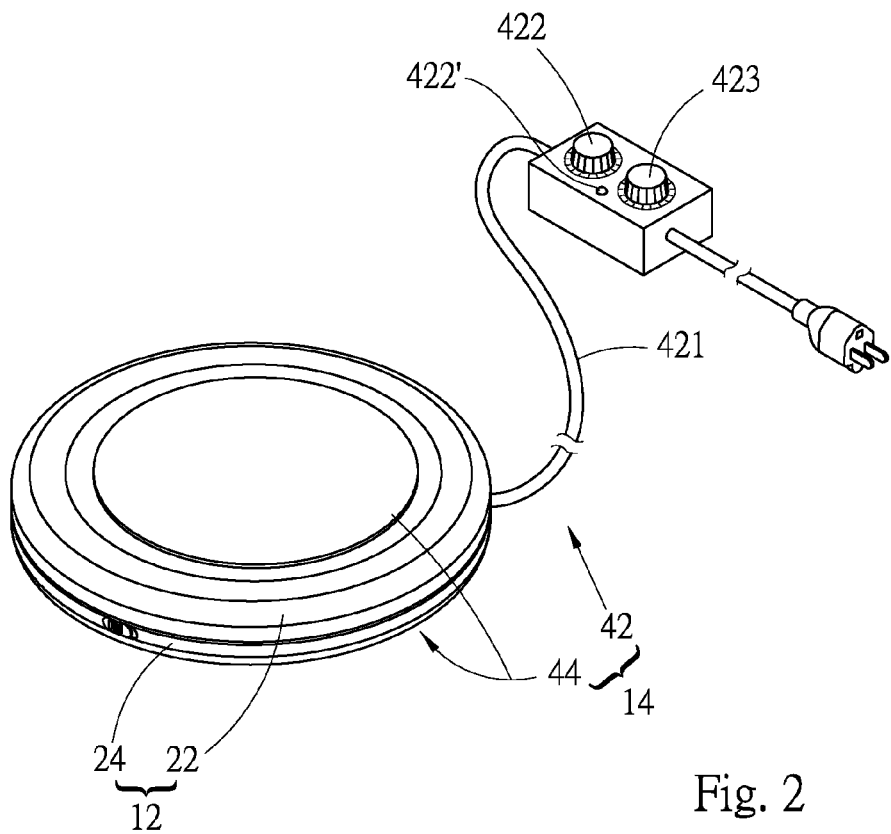
FIG. 2 is a perspective view of a second embodiment of the present invention.

Please refer to FIG. 2, which shows a second embodiment of the present invention. In this embodiment, the heating unit 44 is a resistive electrical heating pad disposed on an outer face of the upper casing 22 and/or an outer face of the lower casing 24. This can also achieve a heating effect.

Figure 3:
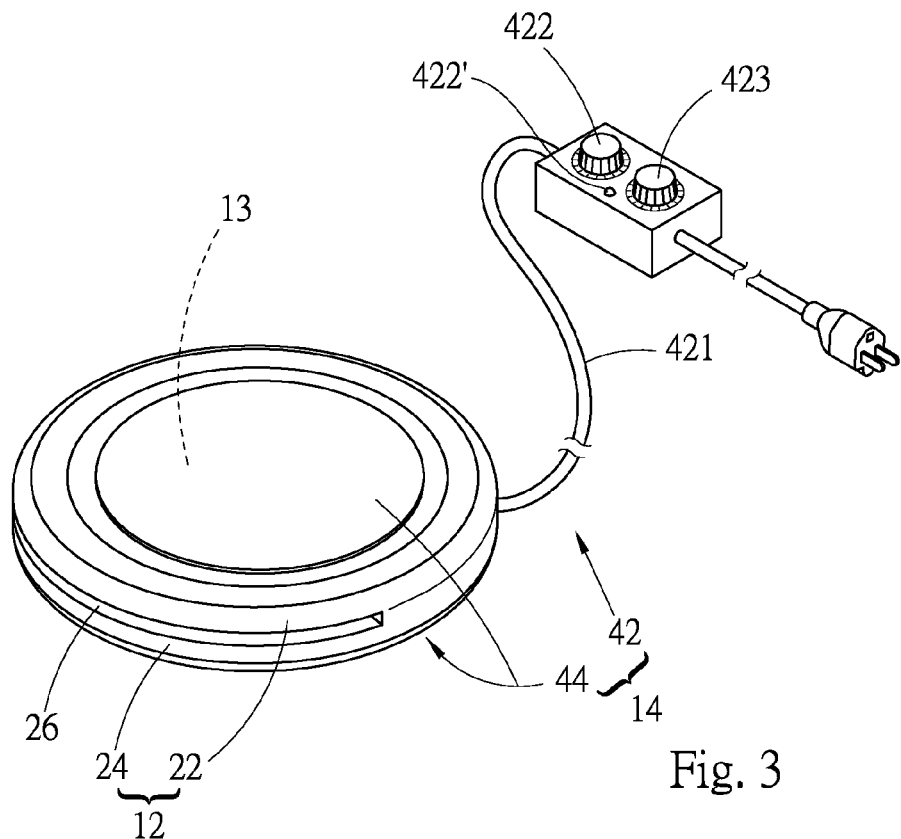
FIG. 3 is a perspective view of a third embodiment of the present invention.

Please refer to FIG. 3, which shows a third embodiment of the present invention. In this embodiment, the case 12 is integrally formed with the upper and lower casings 22, 24 or the upper and lower casings 22, 24 are integrally assembled with each other to form the case 12. One side of the case 12 is formed with a slot or slit 26. The mask (pack) 13 can be inserted, guided or wound into the case 12 through the slot or slit 26. The upper and lower casings 22, 24 also can be a combination of respective components.

Figure 4:
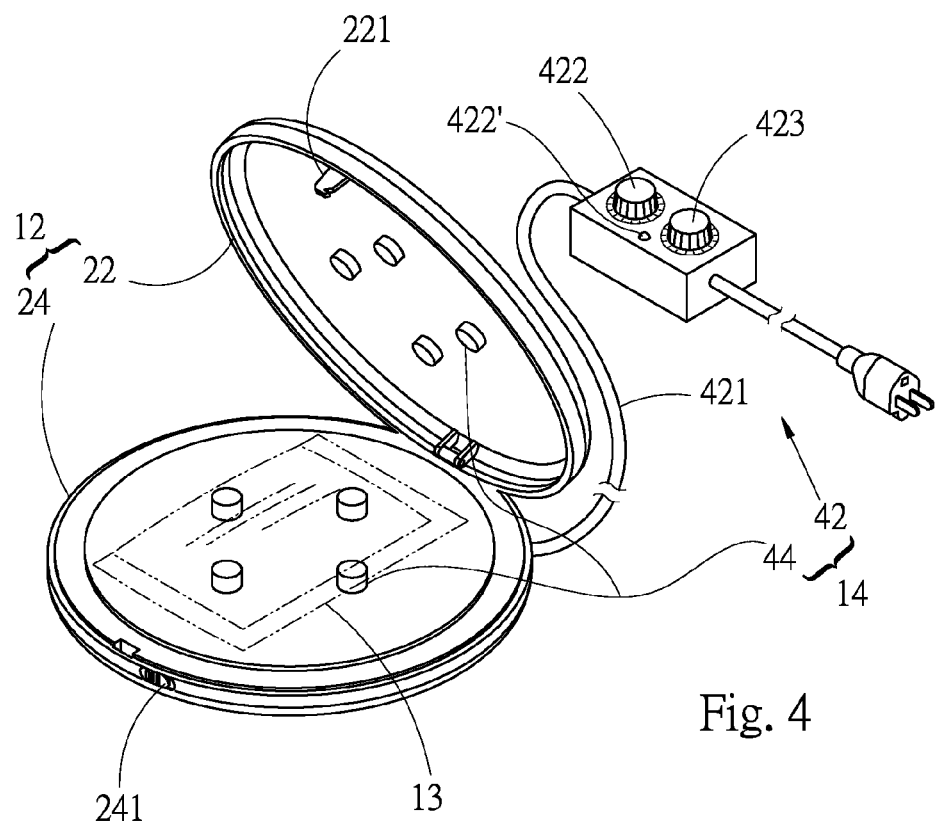
FIG. 4 is a perspective view of a fourth embodiment of the present invention.

Please refer to FIG. 4, which shows a fourth embodiment of the present invention. In this embodiment, the heating unit 44 includes four resistive electrical heating poles disposed on the inner face of the upper casing 22 and/or the inner face of the lower casing 24. The resistive electrical heating poles are in contact with the mask (pack) 13 to provide better heat conduction effect.

Figure 5:
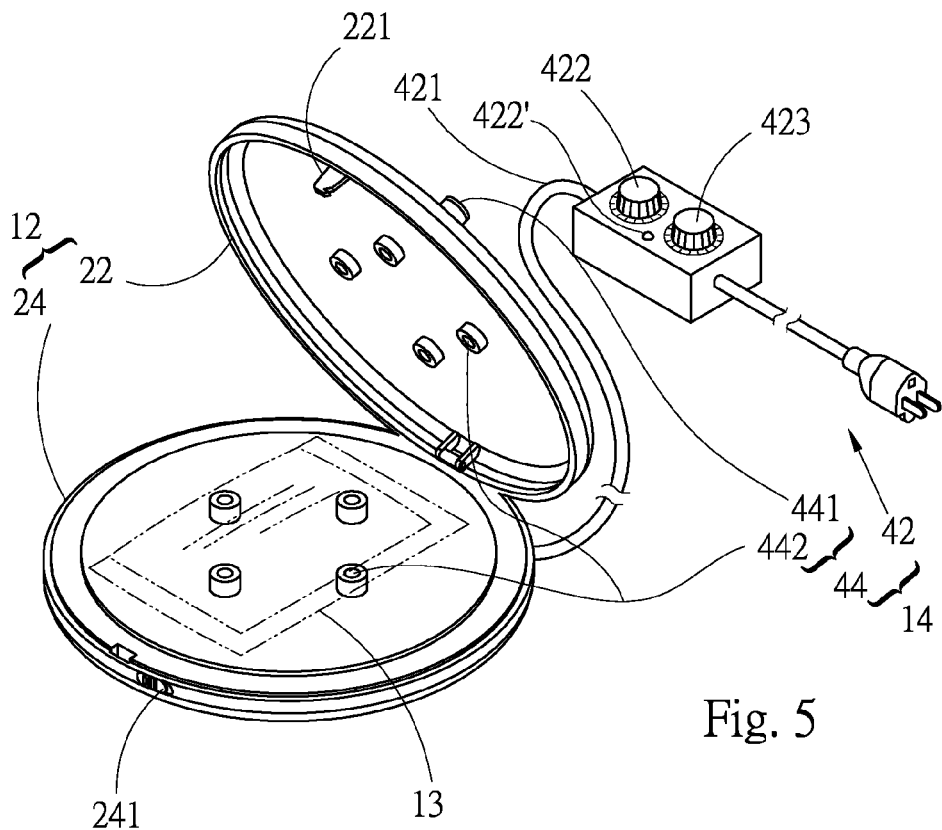
FIG. 5 is a perspective view of a fifth embodiment of the present invention.

Please refer to FIG. 5, which shows a fifth embodiment of the present invention. In this embodiment, the heating unit 44 includes a water inlet 441 and four water vapor holes 442. The case 12 can be further provided with an exhaust port (not shown) for effectively and securely relieving interior pressure of the case 12.

Figure 6:
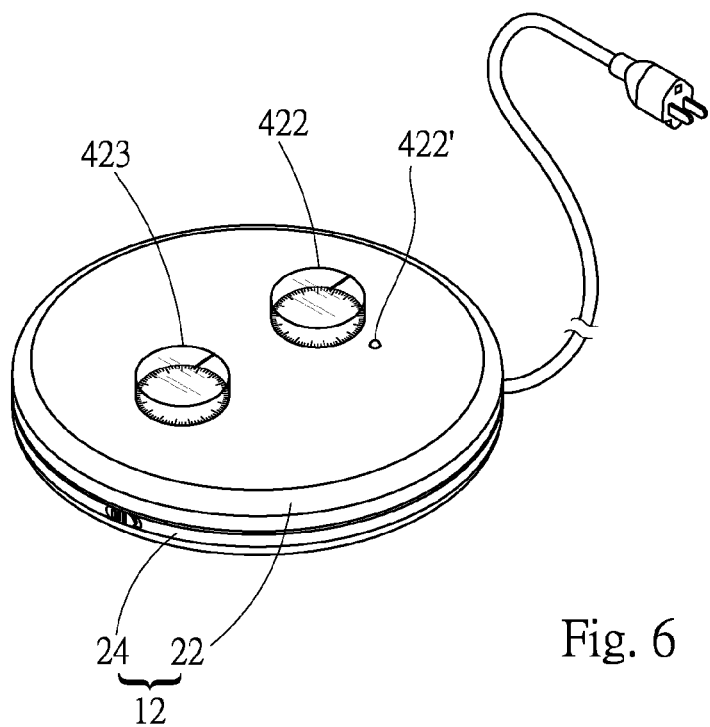
FIG. 6 is a perspective view of a sixth embodiment of the present invention.

Please refer to FIG. 6, which shows a sixth embodiment of the present invention. In this embodiment, the temperature controller 422 and the time controller 423 are positioned on the outer face of the upper casing 22.

Figure 7:
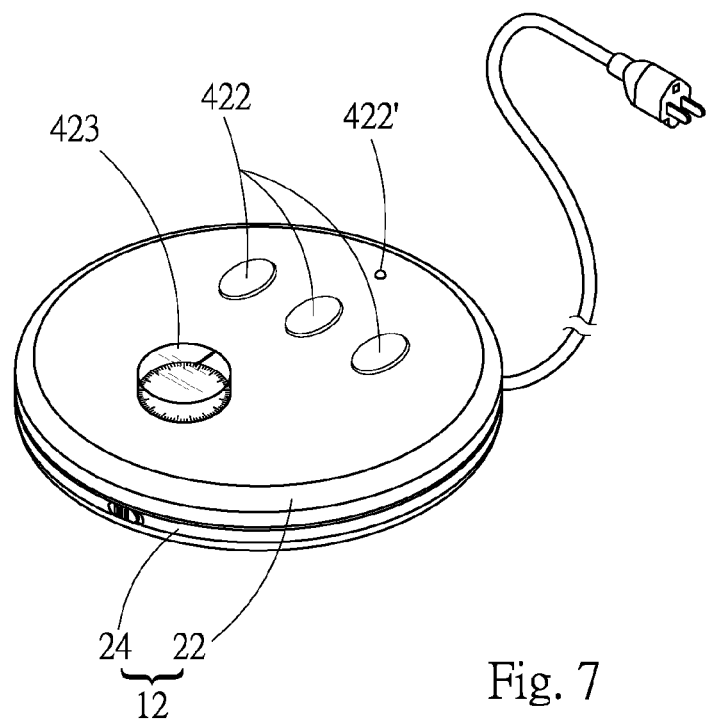
FIG. 7 is a perspective view of a seventh embodiment of the present invention.

Please refer to FIG. 7, which shows a seventh embodiment of the present invention. In this embodiment, the temperature controller 422 includes, for example, three pushbuttons of low temperature 38~39° C., mediate temperature 42~43° C. and high temperature 46~47° C. for selectively controlling the temperature.

Figure 8:
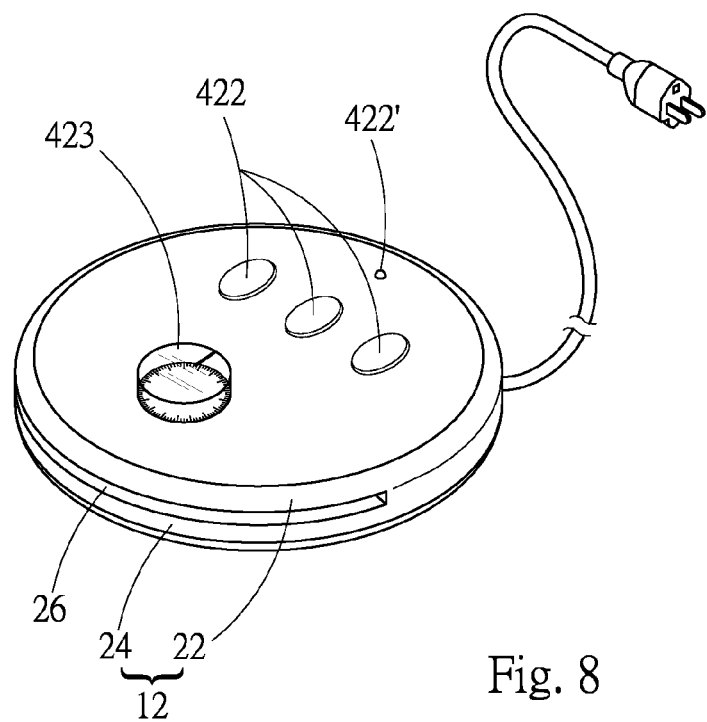
FIG. 8 is a perspective view of an eighth embodiment of the present invention.

Please refer to FIG. 8, which shows an eighth embodiment of the present invention. The eighth embodiment is a modification of the seventh embodiment in which the case 12 is integrally formed with the upper and lower casings 22, 24 or the upper and lower casings 22, 24 are integrally assembled to form the case 12. One side of the case 12 is formed with a slot or slit 26. The mask (pack) 13 can be guided or wound into the case 12 through the slot or slit 26.

In the above embodiment in which the case 12 is integrally formed with the upper and lower casings 22, 24 or the upper and lower casings 22, 24 are integrally assembled to form the case 12, the resistive electrical heating pad can be disposed on the inner face of the upper casing 22 and/or the inner face of the lower casing 24. Alternatively, the resistive electrical heating pad can be disposed on the inner face of the upper casing 22 and/or the outer face of the lower casing 24.

In the human skin mask heating/warming device of the present invention, the temperature controller 422 can include a rotary button or several pushbuttons for freely selectively adjusting the temperature within a range such as 25~75° C. in accordance with the requirements of various skin masks.

In the human skin mask heating/warming device of the present invention, the electrical unit 42 further includes a thermostat with thermostatic function. The thermostat has a thermal sensor. When the temperature selected with the temperature controller 422 descends, the thermal sensor of the thermostat will make the electrical unit 42 further provide a current to the heating unit 44 to keep the temperature selected with the temperature controller 422. Accordingly, the present invention also has warm keeping function. When the electrical unit 42 provides a current, an indicator 422' of the electrical unit 42, such as an LED bulb, will emit light.

In the human skin mask heating/warming device of the present invention, the electrical unit 42 alternatively can be a cell (not shown) for providing a current to the heating unit 44 to generate heat. In this case, the present invention can be more conveniently carried and used.

In the human skin mask heating/warming device of the present invention, the temperature controller 422 and/or the time controller 423 of the electrical unit 42 alternatively can be omitted. This can also achieve the same effect and object of the present invention.

In the market, the mask is generally packaged in a tin foil-made mask pack and soaked in a maintenance solution contained in the pack. The mask pack can be received and heated in the case 12 and the heating unit 44 is able to conveniently and effectively conduct the heat to the mask. Moreover, the temperature or time can be controlled to meet the maintenance requirements of different maintenance solutions.

Figure 9:
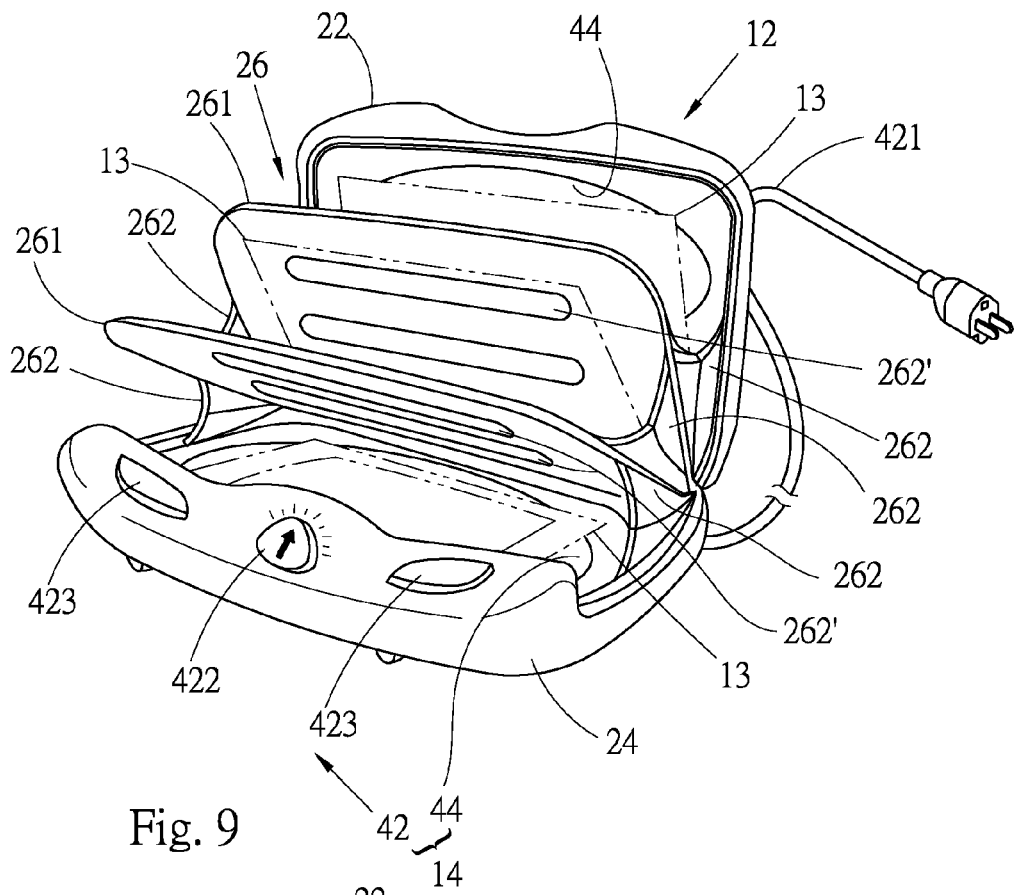
FIG. 9 is a perspective view of a ninth embodiment of the present invention.

Please refer to FIG. 9, which shows a ninth embodiment of the present invention. In the ninth embodiment, the upper and lower casings 22, 24 can be opened or closed to each other. The heating unit 44 can be a resistive electrical heating pad disposed on an inner face of the upper casing 22 and/or an inner face of the lower casing 24. The case 12 further includes a partitioning unit 26 positioned between the upper and lower casings 22, 24 to partition the receiving space therebetween.

The partitioning unit 26 includes two partitioning plates 261 arranged in adjacency to each other and at least three flexible bridge sections 262. One of the bridge sections 262 is positioned between the two partitioning plates 261 with two ends respectively connected with two opposite sides of the two partitioning plates 261. Two ends of each of the other two bridge sections 262 are respectively connected with the inner side of the case 12 and one side of the corresponding partitioning plate 261. Accordingly, when opening the case 12, three sector-shaped receiving spaces are formed for conveniently placing in or taking out the mask (pack) 13. When closing the case 12, the partitioning unit 26 and the mask (pack) 13 are received in the case 12. Each partitioning plate 261 is formed with at least one perforation 261' for enhancing convection in heating process.

The temperature controller 422 can include a rotary button for freely selectively adjusting the temperature within a range such as 25~75° C. The time controller 423 includes two pushbuttons one of which is for turning on the heating unit 44, while the other of which is for turning off the heating unit 44. In other words, the present invention can be manually operated to control the heating time of the heating unit 44. The electrical unit 42 includes a thermostat with thermostatic function.

Figure 10:
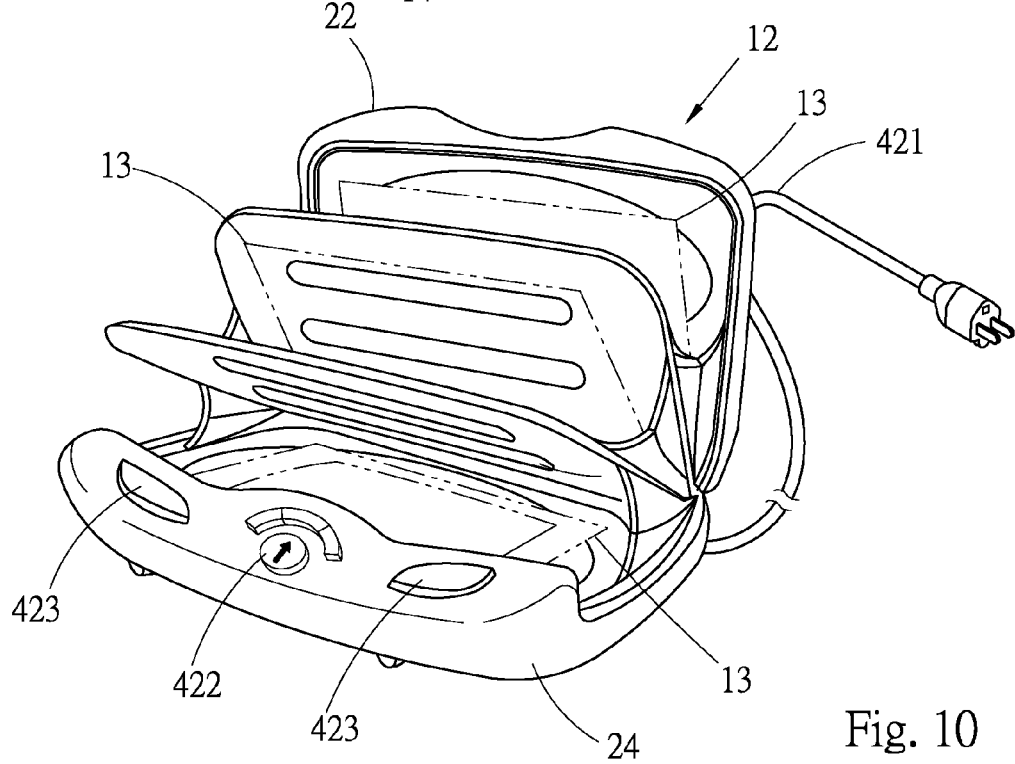
FIG. 10 is a perspective view of a tenth embodiment of the present invention.

Please refer to FIG. 10, which shows a tenth embodiment of the present invention. In the tenth embodiment, the temperature controller 422 can be selectively set at any of three sections respectively indicating one, two or three masks (packs) 13.

In addition, the present invention being used to heat the skin plaster of the traditional Chinese medical science is better than a hairdryer or fire.

The above embodiments are only used to illustrate the present invention, not intended to limit the scope thereof. Many modifications of the above embodiments can be made without departing from the spirit of the present invention.

What is claimed is:

1. A human skin mask heating/warming device comprising:
   a case including an upper casing, a lower casing, and an electrical heating device, a receiving space being defined between the upper and lower casings for receiving therein human skin masks, the electrical heating device being disposed on the case, the electrical heating device at least including an electrical unit and a heating unit, the electrical unit serving to provide a current to the heating unit for generating heat, the heating unit being disposed on the case for providing the heat to the human skin masks;
   wherein the case is selected from a group consisting of a case in which one end of the upper casing is pivotally connected with one end of the lower casing, a case integrally formed with the upper and lower casings and having a slot, and a case in which the upper and lower casings are integrally assembled to form the case with a slot;
   wherein the case with one end of the upper casing pivotally connected with one end of the lower casing further includes a partitioning unit for partitioning the receiving space between the upper and lower casings;
   wherein the partitioning unit includes two partitioning plates arranged in adjacency to each other and at least three flexible bridge sections, one of the bridge sections being positioned between the two partitioning plates with two ends respectively connected with two opposite sides of the two partitioning plates, two ends of each of the other two bridge sections being respectively connected with the inner side of the case and one side of the corresponding partitioning plate, whereby when opening the case, three sector-shaped receiving spaces are formed.

2. The human skin mask heating/warming device as claimed in claim 1, wherein the heating unit is a resistive electrical heating pad disposed between the upper and lower casings or disposed on an outer side of the case.

3. The human skin mask heating/warming device as claimed in claim 1, wherein the heating unit is at least one resistive electrical heating pole disposed between the upper and lower casings.

4. The human skin mask heating/warming device as claimed in claim 1, wherein the heating unit includes a water inlet and at least one water vapor hole, the water inlet being disposed on an outer side of the case, the water vapor hole being disposed between the upper and lower casings.

5. The human skin mask heating/warming device as claimed in claim 1, wherein each partitioning plate is formed with at least one perforation.

6. The human skin mask heating/warming device as claimed in claim 5, wherein the electrical unit further includes a temperature controller for controlling the temperature of the heating unit.

7. The human skin mask heating/warming device as claimed in claim 5, wherein the electrical unit further includes a time controller for controlling heating time of the heating unit.

8. The human skin mask heating/warming device as claimed in claim 1, wherein the electrical unit further includes a temperature controller for controlling the temperature of the heating unit.

9. The human skin mask heating/warming device as claimed in claim 1, wherein the electrical unit further includes a time controller for controlling heating time of the heating unit.

* * * * *